United States Patent [19]

Heikkila et al.

[11] Patent Number: 4,628,726
[45] Date of Patent: Dec. 16, 1986

[54] ANALYSIS OF ORGANIC COMPOUNDS IN BATHS USED IN THE MANUFACTURE OF PRINTED CIRCUIT BOARD USING NOVEL CHROMATOGRAPHIC METHODS

[75] Inventors: Kurt E. Heikkila, Shoreview; Rodney K. Williams, St. Paul; Russell J. Pylkki, Minneapolis, all of Minn.

[73] Assignee: ETD Technology, Inc., Shoreview, Minn.

[21] Appl. No.: 790,834

[22] Filed: Oct. 24, 1985

Related U.S. Application Data

[63] Continuation-in-part of Ser. No. 594,558, Mar. 29, 1984.

[51] Int. Cl.$^4$ ............... G01N 31/08; B01D 15/08
[52] U.S. Cl. ................... 73/61.1 C; 210/656; 436/161
[58] Field of Search ........... 73/61.1 C; 210/101, 210/198.2, 656, 658; 422/70; 436/161

[56] References Cited

U.S. PATENT DOCUMENTS

| | | | |
|---|---|---|---|
| 3,230,048 | 1/1966 | Skeggs | 73/61.1 C X |
| 3,419,051 | 12/1968 | Gustafson et al. | 73/61.1 C X |
| 3,537,585 | 11/1970 | Waters | 210/198.2 |
| 3,551,107 | 12/1970 | Hrdina | 23/230 |
| 3,719,084 | 3/1973 | Walker | 73/23.1 |
| 3,830,369 | 8/1974 | Pfadenhauer | 210/198.2 |
| 3,897,213 | 7/1975 | Stevens et al. | 210/656 X |
| 4,003,243 | 1/1977 | Blu et al. | 73/61.1 |
| 4,047,892 | 9/1977 | Fuller | 436/161 X |
| 4,116,837 | 9/1978 | Biermacher | 210/198.2 |
| 4,132,605 | 1/1979 | Tench et al. | 204/1 T |
| 4,217,223 | 8/1980 | Baba et al. | 210/198.2 |
| 4,233,030 | 11/1980 | Twitchett et al. | 436/161 |
| 4,265,634 | 5/1981 | Pohl | 210/198.2 X |
| 4,314,823 | 2/1982 | Rich, Jr. et al. | 210/198.2 X |
| 4,326,940 | 4/1982 | Eckles et al. | 422/70 X |
| 4,341,634 | 7/1982 | Matsushita et al. | 210/656 |
| 4,364,263 | 12/1982 | Sankoorikal et al. | 73/61.1 |
| 4,377,482 | 3/1983 | Rivier | 210/198.2 X |
| 4,448,691 | 5/1984 | Davis | 210/198.2 X |
| 4,451,374 | 5/1984 | Peterson et al. | 210/198.2 X |
| 4,468,331 | 8/1984 | Antle et al. | 210/198.2 X |
| 4,500,431 | 2/1985 | Miyanaga et al. | 210/198.2 X |

OTHER PUBLICATIONS

Analysis of Organic Components in Copper Plating Baths by Liquid Chromatography, Zatko and Freitag, Sperry Univac, pp. 1-7.

*Primary Examiner*—Robert Spitzer
*Attorney, Agent, or Firm*—Merchant, Gould, Smith, Edell, Welter & Schmidt

[57] ABSTRACT

An accurate repeatable quantitative determination of the concentration of organic composition analytes, breakdown products and organic contaminants in plating baths, and in chemical baths other than the plating bath can be made using a novel high-pressure liquid chromatography apparatus in combination with size exclusion chromatography and total organic carbon analysis.

23 Claims, 4 Drawing Figures

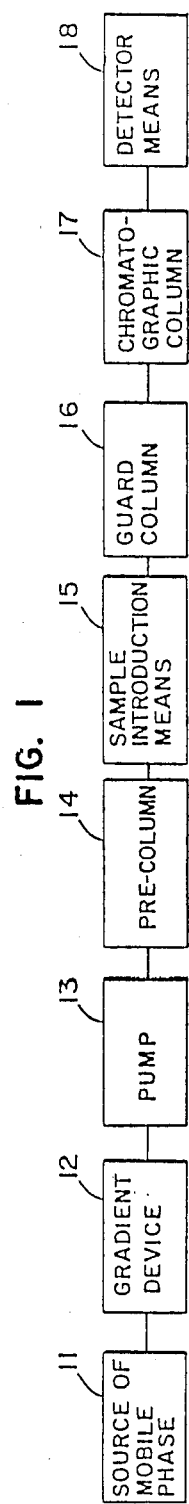
FIG. 1
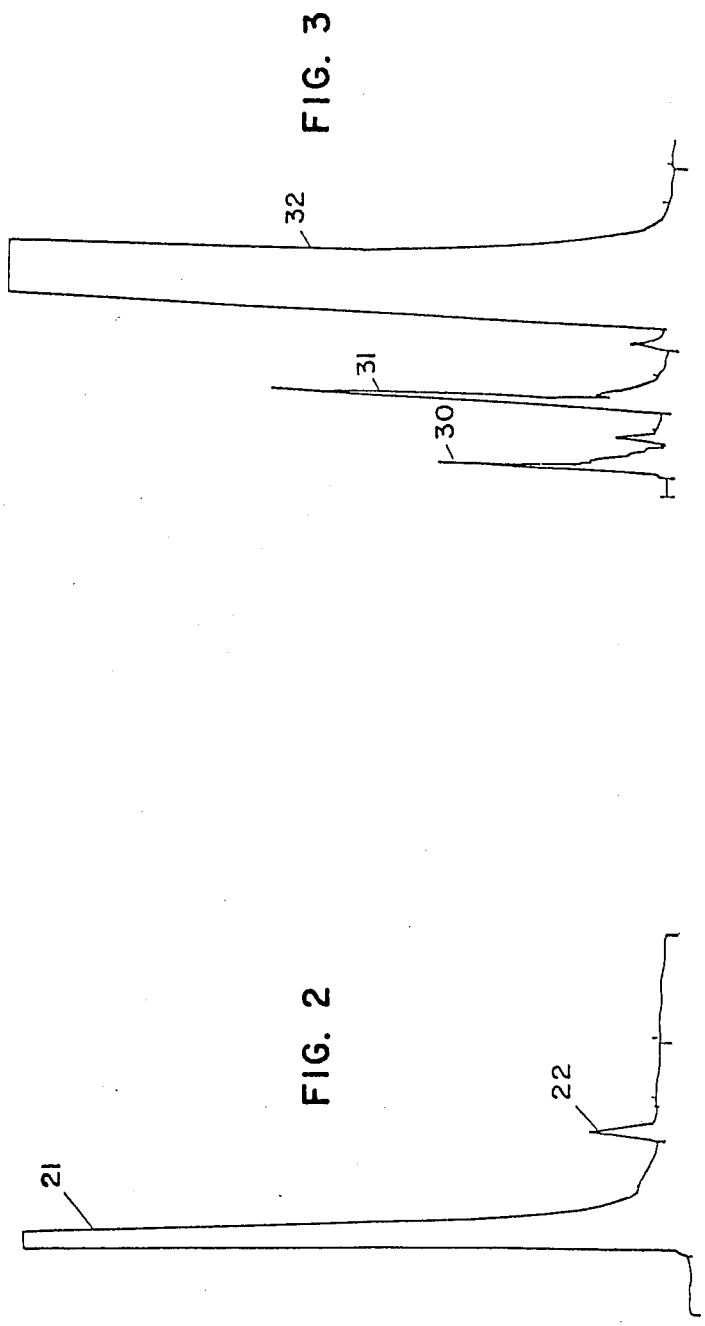
FIG. 3
FIG. 2

ANALYSIS OF ORGANIC COMPOUNDS IN BATHS USED IN THE MANUFACTURE OF PRINTED CIRCUIT BOARD USING NOVEL CHROMATOGRAPHIC METHODS

This application is a continuation-in-part of U.S. Ser. No. 06/594,558 filed Mar. 29, 1984.

FIELD OF THE INVENTION

The invention relates to the quantitative determination of the concentration of organic compounds, their decomposition products and organic contaminants in plating baths and in baths other than plating baths used in the manufacture of printed circuit boards.

BACKGROUND OF THE INVENTION

The advent of printed circuit boards has made possible the efficient assembly of highly complex electronic instruments such as computers, communication equipment, testing equipment, video equipment, etc. Printed circuit boards are commonly planar, flexible or inflexible sheets of material having thin, conductive lines or paths of metal on their surface and in their interior onto which electronic components can be mechanically attached in order to electrically interconnect the electronic components into an active circuit. The further advent of high density, double sided or multi-layered printed circuit boards that are designed to interconnect very large numbers of very large scale integrated circuits, integrated circuits, transistors, resistors, capacitors and other electronic components, required the development of technology for plating metal through holes in the board to interconnect the sides or layers of metal in the high density board.

During the manufacture of such metal clad printed circuit boards and such complex double sided or multi-layered plated-through printed circuit boards, close control over the deposition of copper is required so that neither too much nor too little copper is plated on the board or in the plated-through holes and that the copper deposit has a bright shiny uniform appearance with physical properties of high ductility and tensile strength. Methods for plating copper and other metals on a printed circuit board substrate involve the electro-deposition of a metal in which an electrical plating circuit is formed that causes dissolved copper ions in a plating solution, or plating medium, to combine with electrons on a printed circuit board hole or surface and be reduced to base metal. It has been found that the rate of electrodeposition of a metal from solution is important in order to efficiently and repeatedly form a uniform continuous smooth layer of bright shiny metal having a controlled depth or thickness with the good physical properties. Organic additives, used in electroplating baths, effectively control the rate of metal deposition, maintaining control over the physical properties of the plated metal as well as appearance.

Plating baths commonly contain at least one of two different types of additive. Additive systems can contain up to 10 different organic compounds in an electroplating formulation. A first type of additive is commonly called a brightener. This family of chemical constituents are commonly low molecular weight monomeric compounds which must be maintained in a range of concentration in the plating bath of about 0.1 to 1,000 parts of additive per million parts of plating bath in order to obtain acceptable electrodeposition of the base metal on the printed circuit board. The concentration of brightener can fluctuate due to the electrochemical destruction of the additive and the inclusion of the additive in the copper plate. As the brightener concentration drops, the copper electroplate can become coarse-grained or burned and powdery. In the instance that the brightener concentration is too high, the copper plate can again show a burned deposit with brittle or nonuniform results.

Plating baths can also contain one or more of a polymeric additives which are commonly called a leveler or a carrier. Similarly, the polymeric additives can be electrochemically degraded, mechanically degraded, or thermally degraded, resulting in a distribution of a family of polymeric additive by-products which must be quantified to monitor additive quality.

Plating baths can also derive organic contaminants from a number of sources including degradation products of additives, residual contaminants from other processing steps and the organic material from which the circuit board is made.

Individual contaminants that are derived from other processing steps are commonly virtually any type of organic compound that is carried forward from processing steps upstream of the copper plating bath which become physically or chemically associated with the printed circuit board substrate material. Upstream bath compositions function to clean, condition, etch, activate, accelerate or form the printed circuit board material before copper plating. The baths can contain anionic, nonionic, cationic and ampoteric surfactants, polymeric compositions, organic acids and bases, amines, hydroxy compounds, and many others. These compounds, while functional in the baths upstream of the plating bath, if carried forward into the plating bath can cause substantial reduction in plating efficiency, can alter the smoothness of the resulting copper plate, can reduce the purity of the resulting copper plate, can change the metallurgy of the resulting copper plate, and many other problems. Not only can the compounds which are intentionally placed in the baths upstream of the plating bath cause problems, but contaminants of the upstream baths can also be carried forward into the plating bath, causing similar problems.

Control of the copper plating process can clearly be enhanced by a detailed knowledge of the contents of each upstream bath and a clear detailed knowledge of the effect of the carry forward of bath additives and contaminants into the plating bath itself.

In the past, the quality of the plating medium has been tested using a Hull cell which is a small electrodeposition cell through which a current is passed and the nature of the copper electroplate is observed as it is plated in the cell. The concentration, purity, quantity of degradation or other quality of the additives and bath constituents can be roughly evaluated by viewing the nature of the electrodeposition. However, the Hull cell does not provide a direct measurement of additive concentration. Similarly, Tench, U.S. Pat. No. 4,132,605, teaches an electrical voltametric method of monitoring the concentration of additives by measuring the amount of copper plated or removed during a voltametric cycle. In this test the nature and amount of copper plated in the electrical test cell is observed but a direct measurement of the concentration of specified organic additive is not done. I am also aware that Zatco and others have attempted an analysis of organic components of copper plating baths using high pressure liquid chromatography techniques (70th AES Conference, June 1983). Our attempts to perform a reproducible quantitative routine analysis of the organic additives using the Zatco-type methods have not succeeded. We believe that the extremely corrosive, acidic or basic nature of plating baths, that we have attempted to analyze, interfere substantially with the chromatography columns used in the HPLC apparatus.

In liquid chromatography, more particularly high pressure liquid chromatography (HPLC), the sample to be analyzed is placed on the end of a column that commonly contains a silica support which is chemically or physically associated with a stationary phase. A solvent or mobile phase is directed through a chromatographic column and carries the sample over the stationary phase. The differences in affinity between the components of the analyzed material and the stationery phase on the support causes the components in the sample to separate, or be resolved, as the solvent carries the material through the column. The most common column support material is a silica composition which has the drawback that it can interact with both acidic or basic components of the plating bath, resulting in substantial interference with the separation of free components in the chromatographic column. We have attempted a prechromatographic neutralization of the acidic and basic components of the plating bath with a variety of techniques, but have found that the formation and removal of the resulting neutralization products or salts can cause substantial loss of organic material and the neutralization products can cause an unwanted interaction with the silica support during chromatographic analysis.

Accordingly, a substantial need exists for a reproducible, precise, accurate, routine HPLC method which suffers no interference from the highly corrosive acidic or basic nature of the bath, for the analysis of individual and collective organic constituents in electroplating baths and baths upstream of the plating baths that can be rapidly and routinely performed on a day to day basis to determine the types and state of the organic additives in a plating bath. Further such an HPLC method is essential if size exclusion chromatography, total organic carbon analysis and HPLC are to be successfully used to accurately reflect the total state of the plating bath organic constituent. These types of chromatographic techniques lend themselves very well to individual component control in terms of a feedback system for automated addition to allow consistent bath performance.

BRIEF DISCUSSION OF THE INVENTION

We have found that the concentration of organic brightener additive constituents of plating baths and the concentration of organic compounds in baths upstream of the plating bath can be rapidly and routinely determined using an HPLC apparatus that comprises a source of solvent under pressure, a precolumn sample introduction means, a guard column containing the analytical column material that can absorb, neutralize, or otherwise render innocuous acidic, basic or other constituents of the bath sample harmful to the analytical chromatographic column, a chromatographic column for the separation or resolution of the organic constituents of the bath sample, and a detection means which can detect and display some measurement of the concentration of the organic constituents. A second column can be placed prior to the sample injection means containing a silica composition that can saturate the mobile phase with dissolved silica and can act to reduce dissolution of silica in the guard column and chromatographic column. One aspect of the invention lies in the analysis of baths, upstream of the plating bath, which prepare the printed circuit board material for plating by introducing an untreated sample of the bath medium into the HPLC apparatus of the invention. Another aspect of the invention resides in a method for the analysis of plating bath or upstream baths which comprises introducing an untreated sample of the plating media into the HPLC apparatus of the invention. A further aspect of the invention resides in the determination of the state of all organic bath constituents including determination of brightener concentration, molecular weight, distribution of leveler, organic contaminant concentration, etc. with a combined use of size exclusion chromatography, total organic carbon analysis and the novel HPLC method.

BRIEF DESCRIPTION OF THE DRAWINGS

FIG. 1 shows a block flow chart diagram of a preferred embodiment of the invention.

FIG. 2 shows a computer generated chart, recording the results of an analysis of a copper plating bath.

FIG. 3 shows a computer generated chart recording the analysis of a commercial brightener additive concentrate composition.

DETAILED DESCRIPTION OF THE INVENTION

Figure 4:
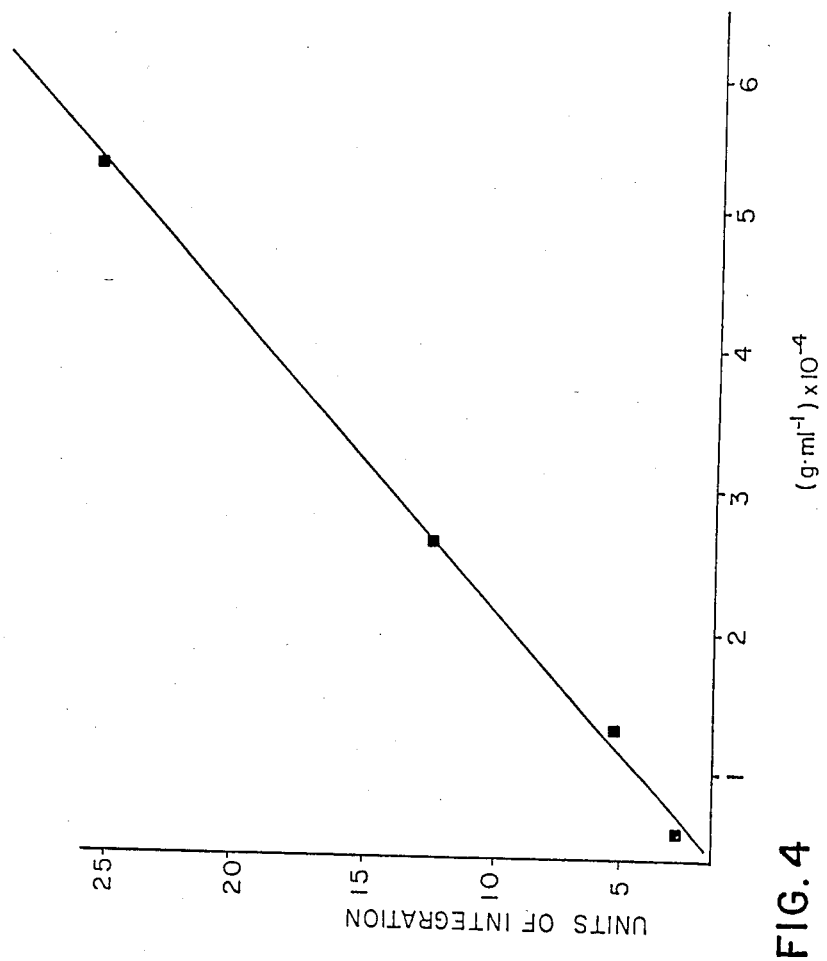
FIG. 4 shows that the high pressure liquid chromatography technique of the invention produces a linear relationship between additive concentration and the arbitrary integration units produced at the detection means.

A guard column which can be used in the apparatus and method of the invention to analyze bath media used in the manufacture of metal clad printed circuit boards commonly comprises a flexible or inflexible tube made of plastic, ceramic, metal, glass or other material having dimensions of about 1 to 100 centimeters in length, and about 0.1 to 15 millimeters in inside diameter. The guard column commonly contains the same packing material as the analytical column (discussed below) which can absorb, interact with, neutralize or otherwise render innocuous the highly corrosive acidic, basic or otherwise harmful constituents of the plating bath and baths upstream of the plating bath. The packing material is retained within the column using commonly available retention means. At the inlet and the outlet of the guard column is installed commonly available means for attaching the guard column in liquid communication with other apparatus components. The guard column when used in conjunction with the precolumn (discussed below) which can saturate the mobile phase with silica, introduces reproducibility and stability into the chromatographic system for bath analysis.

The nature of the packing material in the guard column is important in order to result in substantial removal of the acidic or basic components of the plating bath while maintaining sufficient solvent flow and reducing pressure drop across the analytical column. The support material should be of sufficiently small particle size to present sufficient surface area for complete interaction between the acidic and basic components and the packing material. However, the particle size of the silica should be large enough to prevent the tendency of relatively small particles to plug and reduce the permeability of the chromatographic column increasing the pressure drop across the precolumn. Accordingly, the packing material should have a particle size of 2 to 100 microns, preferably 5 to 20 microns, and most preferably, for reasons of low cost, high component resolution, and low pressure drop, 3 to 10 microns.

Attached to the guard column inlet in liquid communication is the outlet of a sample introduction means. The sample introduction means commonly is an apparatus which permits the introduction of a highly accurate but very small volume of a liquid sample into the high pressure liquid chromatography apparatus. A broad variety of known sample introduction means can be used. Most commonly, sample injection means are used into which a hypodermic needle can be introduced to deposit the to-be-analyzed sample into the solvent stream. The sample introduction can be made using a solvent diverting valve which can allow introduction by flowing the solvent through a sample loop of the injection valve. Commonly the sample size can range from about 1 to 1,000 microliters (uL). The outlet end of the sample introduction means is attached to the inlet of the guard column in liquid communication. The sample is inserted into the mobile phase at the sample introduction means which carries the sample first into the guard column and then into the chromatographic column.

The solvent or mobile phase is generated by a source of solvent under pressure. The solvent can be a single phase aqueous solvent or organic solvent. Alternatively, the solvent can comprise a mixture of organic and aqueous phases in constant proportion or can have the aqueous and organic components in continual varying concentration as the solvent passes through the HPLC. Using the single phase solvent, the source of solvent commonly comprises a container of solvent in liquid communication with a pump that can generate pressures from about 1–10,000 pounds per square inch (psi) and can deliver the solvent under pressure and a controlled flow rate from 0.01 to 5.0 ml/min to the inlet of the sample introduction means. In the instance a mixed solvent having a fixed solvent ratio or a mixed solvent of continually varying component concentrations is needed, the source of solvent comprises two containers of differing solvents, a gradient device in liquid communication with the two containers which mixes the solvents in proportions as programmed by the operator. The solvents then are transferred from the gradient device to the pump where pressure is increased for application to the sample introduction means. Preferred pressures for the HPLC apparatus can range from about 100–5,000 psig and most preferably, for ease of use and high resolution, pressures can range from about 200–3,500 psig.

Attached to the guard column outlet in liquid communication is a chromatographic column having an inlet and an outlet. The chromatographic column can be a tube made of plastic, ceramic, metal, glass or other material having dimensions of about 1 to 100 centimeters in length and about 0.1 to 15 millimeters in inside diameter. The chromatographic column commonly contains a packing which comprises an inert support material which is physically coated or chemically bonded to a stationary phase and can contain other material. The support material is of a particle size which is sufficiently small to present sufficient surface area for efficient resolution of additive components but is of large enough size that the column is permeable to the flow of solvent and does not plug. Relatively small particle size support material can plug the column and reduce the permeability of the chromatographic column. Accordingly, the support material has a particle size of 2 to 100 microns, preferably 2 to 20 microns, and most preferably for reasons of low cost and high component resolution 3 to 10 microns.

The stationary phase which interacts with the analyzed material in the presence of the mobile phase to resolve the analyte materials is commonly an organic material which is physically coated or chemically bonded to the stationary phase. The stationary phases are commonly silica to which specific moieties have been chemically bonded (phenyl, octadecyl, octyl, dimethyl, amino, nitrile, diol, etc. are typical moieties). Preferred stationary phases for use in the high pressure liquid chromatography apparatus of this invention comprise $C_{6-24}$ aliphatic hydrocarbons chemically bonded to the support. These stationary phases are available as reacted supports or as a prepacked commercial analytical columns.

The outlet of the chromatographic column is commonly connected in liquid communication with a detector means. The detector means commonly comprises a cell which can measure the ultra-violet absorbance, refractive index, thermal or electrical conductivity, electrochemical activity, or other indication of the relative concentration resolved component in the mobile phase as it flows through the cell. Such characteristics are electronically monitored and are read out onto a recording chart, stored by electronic or computer components, or otherwise recorded. A combination of the above detectors or monitors can be used to determine the presence and relative concentration of each resolved additive component as it flows through the cell.

The preferred HPLC apparatus of the invention contains a precolumn means inserted in fluid communication between the pump and the sample introduction means. The purpose of the precolumn means is to condition the solvent with dissolved silica to prevent dissolution of silica support in the guard and chromatographic columns. The silica material in the guard and the chromatographic columns has a small but finite solubility in a variety of the solvent systems used as the mobile phase in the HPLC apparatus and method. The stability of the chromatographic column is of primary importance since minor changes in the column can result in major inaccuracy. The precolumn contains silica which comes in contact with the mobile phase as it passes through the precolumn and dissolves into the mobile phase at a known or measurable rate. Since the rate of dissolution of silica into the solvent stream is known, the precolumn can be changed at predetermined intervals to insure that the solvent stream is continually conditioned for accurate chromatography. The precolumn can commonly comprise a flexible or inflexible tube, containing a silica composition, made of plastic, ceramic, metal, glass or other material having dimensions of about 1 to 100 centimeters in length and about 0.1 to 10 millimeters in inside diameter. The precolumn can contain a silica material identical with the analytical column packing or can contain a silica composition essentially free of the stationary phase material. The precolumn packing material is retained within the column using commonly available retention means. At the inlet and outlet of the precolumn is installed commonly available means for attaching the precolumn in liquid communication with the ample introduction means and the pump.

Similarly with the packing material in the guard column and the chromatographic column the stationary phase packing material is selected to maintain sufficient solvent flow and to reduce pressure drop across the column. The stationary phase packing should be of sufficiently small particle size to present sufficient surface area for dissolution of silica material, however the particle size of the stationary phase should be large enough to prevent the tendency of the relatively small particles of stationary phase to plug and reduce the permeability of the chromatographic column thus increasing pressure drop across the guard column. Accordingly the packing material should have a particle size of 2 to 20 microns, and most preferably for reasons of low cost, high component resolution and low pressure drop, of about 3 to 10 microns.

The mobile phase after detection commonly flows into a waste collection system.

Aqueous solvents useful in the HPLC apparatus and method commonly comprise well known buffers adjusted to closely control the pH for maximum resolution of components. The aqueous phase can also contain an ion paring agent which will shift the ionic equilibria between the analyte and the column support to aid in enhanced resolution. Many organic solvents such as acetonitrile, methanol, ethanol, tetrahydrofuran and others are organic solvents and have utility in the invention. Preferred organic solvents include acetonitrile and tetrahydrofuran, etc. A mobile phase used in the HPLC apparatus and method can be a mixed aqueous organic solvent wherein the solvent contains about 1 part of aqueous solvent per each 0.01 to 100 parts of organic solvent.

The high pressure liquid chromatography apparatus can be programmed so that a stream of solvent of continually varying proportion between organic and aqueous phases can be applied to the sample introduction means. The above high pressure liquid chromatography apparatus is primarily adapted to the quantitative determination of relatively low molecular weight brightener organic compounds having a molecular weight of less than about 2,000. Higher molecular weight polymeric constituents are most commonly analyzed after separation from the plating media using size exclusion chromatography (SEC) which provides an accurate measurement of polymer size and size distribution.

Further information can be derived from the analysis of plating media by measuring the total organic carbon content of the media. A typical total organic carbon analysis is detailed in method 4.15.1, "Methods for chemical analysis of water and wastes", EPA-600/479-020, EMSL, Cincinnati, (1979). A combination of the high pressure liquid chromatography analysis, the size exclusion chromatography analysis, and the total organic carbon analysis of plating baths and other baths upstream of the plating bath provide a highly accurate control scheme enabling plating operators to monitor plating bath additions and to optimize the plating quality of the metal deposit. Using these monitoring systems, the concentration of brightener can be made, molecular weight distribution of the polymeric constituents can be made, and a determination of the contamination of the plating bath by other organic constituents can be made by subtracting a known brightener concentration and the polymer concentration from the total organic determination value. Using these data, it no longer is guesswork to determine when a plating bath requires treatment to add or remove organic constituents or to replace or replenish additives with fresh material for consistent plating bath performance.

DESCRIPTION OF PREFERRED EMBODIMENT OF HIGH PRESSURE LIQUID CHROMATOGRAPHY APPARATUS

A Hewlet Packard 1084B liquid chromatograph was equipped with a chromatographic column 4.0 mm in inside diameter and 250 millimeters in length. The chromatographic column contained packing comprising a silica support having approximately 1 gram of a $C_{18}$ alcohol chemically bonded to the silica hydroxyl groups (in an octadecyl silyl bonded phase).

Attached to the inlet of the chromatographic column in fluid communication was the outlet of a guard column containing 0.1 gram of the same packing of the analytical column. The inlet of the guard column was attached in fluid communication with the outlet of a sample injection system having an injection volume of 10 microliters. Attached to the inlet of the sample injection valve is the outlet of a precolumn containing a silica packing. Attached to the inlet of the precolumn was a source of solvent under pressure. A mixed aqueous mobile phase was used which comprised in the aqueous phase a 0.01 molar $KH_2PO_4$ buffer of pH 2.3 and an organic phase comprising acetonitrile. A solvent means was programmed to permit solvent flow at the rate of 1.0 milliliters per minute and to mix the organic and aqueous phase at a ratio of about 10 parts of organic phase per 100 parts of total solvent flow. A solvent column and precolumn were maintained at 50° C. The chromatograph used an ultraviolet light detector adjusted to a wavelength of 205 nM.

DETAILD DESCRIPTION OF THE DRAWINGS

FIG. 1 shows a block diagram of a preferred embodiment of the high pressure liquid chromatography of this invention. The source of solvent, or mobile phase, 11 comprises two containers, one having an organic solvent and the other an aqueous solvent. The gradient device 12 mixes the aqueous and organic solvents at constant or varying ratios and delivers the mixture to a pump 13 which provides high pressure for the chromographic analysis. The mobile phase passes through a precolumn 14 which saturates the mobile phase with silica. The sample is injected into the high pressure liquid mobile phase at the sample introduction means 15 and carried to the guard column 16. The guard column packing absorbs substantially all the highly acidic, basic or otherwise harmful components in the sample and the balance of the sample passes from the guard column into the chromatographic column 17. The interaction between the organic constituents of the sample and the stationary phase in the presence in the mobile phase resolves the sample into detectable segments which are detected in the detector 18.

FIG. 2 shows an analysis of a plating bath having two major peaks. The first peak 21 comprises very small amounts of inorganics such as $CuSO_4$, $H_2SO_4$, $Cl^-$, which remain after treatment in the guard column and the second peak 22 is the organic brightener component.

FIG. 3 shows a high pressure liquid chromatographic analysis of a commercial brightener additive. The analysis shows that it has three major components 30, 31 and 32.

FIG. 4 shows that the high pressure liquid chromatography analysis of the brightener in the plating bath has a linear relationship between the concentration of additive and integration units.

I have shown that using the high pressure liquid chromatography method and apparatus of this invention in combination with a total organic carbon analysis and a size exclusion chromatography or gel permeation chromatography analysis, the nature of the bath additives, particularly in the plating bath, and in baths upstream of the plating bath, can be monitored. The concentration of the brighteners or levelers can be measured, the molecular weight distribution of the polymer can be monitored for the creation of low molecular weight species from the high molecular polymer, and the total organic concentration of the bath can be measured using the total organic carbon analysis to yield a measure of plating bath contaminants. Further the source of unknown contaminants can be traced to upstream baths, to the board substrate material or to the bath addition. With such monitoring the concentration of the additives can be augmented or the organic constituents of the bath can be removed by peroxide or other treatment before any adverse effects result on the printed circuit board.

The specification and Drawings are illustrative of the invention. However, since the invention can have many embodiments without departing from the spirit and scope of the invention, the invention resides solely in the claims hereinafter appended.

We claim:

1. An analytical method of determining the concentration of an organic analyte or mixtures thereof in a chemical bath, other than an acidic or basic metal plating bath medium, used in the manufacture of printed circuit boards using an HPLC apparatus having components that maintain the stability, precision and accuracy of the analytical method which comprises:

(1) obtaining an HPLC apparatus having:
  (a) a chromatographic column, containing a stationary phase and a support phase composition sufficient to resolve each organic analyte, having an inlet and an outlet;
  (b) a detector means for measuring the relative concentration of each organic analyte, having an inlet and an outlet, wherein the chromatographic column outlet is attached in liquid communication to the detector inlet;
  (c) a second column, having a packing comprising at least a support phase composition, and having an inlet and an outlet, wherein the second column outlet is connected in liquid communication with the chromatographic column inlet, wherein the second column support phase composition can substantially reduce the effect of the acidic or basic components of the sample on the reproducibility, precision or accuracy of the analysis;
  (d) a sample introduction means having an inlet, an outlet and a sample introduction port, wherein the sample introduction means outlet is attached in liquid communication to the second column inlet; and
  (e) a source of solvent under pressure attached in liquid communication to the sample introduction means inlet;
(2) passing a stream of solvent under pressure through the HPLC apparatus;
(3) applying a sample of the chemical bath to be analyzed into the stream of solvent under pressure at the sample introduction port;
(4) passing the chemical bath sample in the solvent through the second column wherein the column packing substantially reduces the effect of the acid or basic components of the sample, forming an innocuous analyte;
(5) passing the innocuous analyte in the stream of solvent into the chromatographic column, resolving the analyte components into detectable segments utilizing the interaction between the analyte and the stationary phase; and
(6) passing the detectable segments in the solvent into a detector that can produce a signal which as a result of the cooperation of the elements of the HPLC apparatus detector and the sample obtains a substantially linear relationship between the analyte concentration in the sample and the integration units produced from the signal.

2. The method of claim 1 wherein the chemical bath is used in a copper plating process.

3. The method of claim 1 wherein between the source of solvent and the sample introduction means is placed a third column having sufficient support phase to saturate the solvent with dissolved support phase.

4. The method of claim 3 wherein the third column support phase is a silica having a particle size of about 2 to 20 microns.

5. The method of claim 1 wherein the second column support phase has a particle size of about 2 to 20 microns.

6. The method of claim 1 wherein the chromatographic column support phase is a silica and the stationary phase is a $C_{6-24}$ aliphatic hydrocarbon chemically bonded to the silica, wherein the silica has a particle size of 2 to 20 microns.

7. The method of claim 1 wherein the source of solvent under pressure comprises at least one or more solvent containers, a gradient device that can provide a mixture of solvent under constant or varying ratio, and a pump which can provide a solvent flow of 0.01 milliliters per minute to 10 milliliters per minute at a pressure of about 1 to 10,000 psi.

8. The method of claim 7 wherein the source of solvent supplies solvent at a flow rate of about 0.01 to 100 milliliters per minute.

9. The method of claim 8 wherein the solvent is a mixed aqueous organic solvent and wherein the organic phase is acetonitrile, an alcohol, tetrahydrofuran or mixtures thereof.

10. The method of claim 1 wherein the sample introduction means has a sample size of about 1 to 200 microliters.

11. The method of claim 1 wherein the detector means detects the relative absorption of ultraviolet light by the organic analyte.

12. The method of claim 1 wherein the plating bath medium is also analyzed for polymer size distribution and total organic carbon.

13. An analytical method of determining the concentration of an organic analyte or mixtures thereof in a chemical bath, other than an acidic or basic copper plating bath medium, used in the manufacture of printed circuit boards using an HPLC apparatus having components that maintain the stability, precision and accuracy of the analytical method which comprises:

(1) obtaining an HPLC apparatus having:

(a) a chromatographic column, containing a stationary phase and a support phase composition sufficient to resolve each organic analyte, having an inlet and an oulet;

(b) a detector means for measuring the relative concentration of each organic analyte having an inlet and an outlet wherein the chromatographic column outlet is attached in liquid communication to the detector inlet;

(c) a second column, having a packing comprising at least a support phase composition, and having an inlet and an outlet, wherein the second column outlet is connected in liquid communication with the chromatographic column inlet, wherein the second column support phase composition can substantially reduce the effect of the acidic or basic components of the sample on the reproducibility, precision or accuracy of the analysis;

(d) a sample introduction means having an inlet, an outlet and a sample introduction port, wherein the sample introduction means outlet is attached in liquid communication to the second column inlet; and (e) a source of solvent under pressure attached in liquid communication to the sample introduction means inlet;

(2) passing a stream of solvent under pressure through the HPLC apparatus;

(3) applying a sample of the chemical bath to be analyzed into the stream of solvent under pressure at the sample introduction port;

(4) passing the chemical bath sample in the solvent through the second column wherein the column packing substantially reduces the effect of the acid or basic components of the sample, forming an innocuous analyte;

(5) passing the innocuous analyte in the stream of solvent into the chromatographic column, resolving the analyte components into detectable segments utilizing the interaction between the analyte and the stationary phase; and (6) passing the detectable segments in the solvent into a detector that can produce a signal which as a result of the cooperation of the elements of the HPLC apparatus detector and the sample obtains a substantially linear relationship between the analyte concentration in the sample and the integration units produced from the signal.

14. The method of claim 13 wherein between the source of solvent and the sample introduction means is placed a third column having sufficient support phase to saturate the solvent with dissolved support phase.

15. The method of claim 14 wherein the third column support phase is a silica having a particle size of about 2 to 20 microns.

16. The method of claim 13 wherein the second column support phase has a particle size of about 2 to 20 microns.

17. The method of claim 13 wherein the chromatographic column support phase is a silica and the stationary phase is a $C_{6-24}$ aliphatic hydrocarbon chemically bonded to the silica, wherein the silica has a particle size of 2 to 20 microns.

18. The method of claim 13 wherein the source of solvent under pressure comprises at least one or more solvent containers, a gradient device that can provide a mixture of solvent under constant or varying ratio, and a pump which can provide a solvent flow of 0.01 milliliters per minute to 10 milliliters per minute at a pressure of about 1 to 10,000 psi.

19. The method of claim 13 wherein the sample introduction means has a sample size of about 1 to 200 microliters.

20. The method of claim 13 wherein the detector means detects the relative absorption of ultraviolet light by the organic analyte.

21. The method of claim 13 wherein the plating bath medium is also analyzed for polymer size distribution and total organic carbon.

22. The method of claim 13 wherein the source of solvent supplies solvent at a flow rate of about 0.01 to 100 milliliters per minute.

23. The method of claim 22 wherein the solvent is a mixed aqueous organic solvent and wherein the organic phase is acetonitrile, an alcohol, tetrahydrofuran or mixtures thereof.

* * * * *